United States Patent [19]

Kummer et al.

[11] 3,980,670

[45] Sept. 14, 1976

[54] MANUFACTURE OF METHACRYLIC ACID AND BUTYROLACTONE

[75] Inventors: Rudolf Kummer, Frankenthal; Rolf Platz, Mannheim; Kurt Schwirten, Ludwigshafen, all of Germany

[73] Assignee: BASF Aktiengesellschaft, Ludwigshafen (Rhine), Germany

[22] Filed: Feb. 25, 1975

[21] Appl. No.: 552,734

[30] Foreign Application Priority Data

Mar. 11, 1974  Germany............................ 2411440

[52] U.S. Cl............................ 260/343.6; 260/526 N
[51] Int. Cl.² ........................................ C07D 307/32
[58] Field of Search......... 260/343.6, 526 N, 530 R, 260/530 N, 535 R, 491

[56] References Cited
FOREIGN PATENTS OR APPLICATIONS 2,106,243  8/1972  Germany ........................ 260/343.6
2,247,650  4/1973  Germany ........................ 260/343.6

*Primary Examiner*—Natalie Trousof
*Assistant Examiner*—C. M. S. Jaisle
*Attorney, Agent, or Firm*—Johnston, Keil, Thompson & Shurtleff

[57] ABSTRACT

Methacrylic acid and butyrolactone are manufactured by hydroformylation of allyl esters of lower carboxylic acids in the presence of rhodium catalysts and inert organic solvents, followed by oxidation of the resulting formyl compounds with molecular oxygen (e.g. with air) in the presence of lower fatty acids, without prior removal of the rhodium catalysts, and elimination of the carboxylic acid from the acyloxybutyric acids formed, at from 150° to 500°C, using catalysts such as aluminum oxide, silicates or active charcoal.

8 Claims, No Drawings

MANUFACTURE OF METHACRYLIC ACID AND BUTYROLACTONE

The present invention relates to a new process for the manufacture of methacrylic acid and butyrolactone.

Methacrylic acid and butyrolactone are important starting materials in the chemical industry. Methacrylic acid has hitherto been manufactured industrially from acetone and hydrocyanic acid; in this process, substantial amounts of ammonium sulfate are formed as a waste product in the hydrolysis stage. Butyrolactone - an important solvent - is obtained by manufacturing butynediol from acetylene and formaldehyde, hydrogenating it to butanediol and converting the latter to butyrolactone. However, acetylene is increasingly becoming a less attractively priced starting material for chemical products. Whilst German Published application 2,106,243 discloses the hydroformylation of allyl acetate in the presence of rhodium catalysts, this reaction exclusively gives methacrolein, and the oxidation thereof to methacrylic acid by conventional methods proves very unsatisfactory (cf. German Published application 2,247,650).

It is an object of the present invention to provide a process whereby methacrylic acid and butyrolactone may be obtained more easily in an industrial scale.

We have found that methacrylic acid and butyrolactone are obtained advantageously by a process wherein allyl esters of lower fatty acids are hydroformylated by conventional methods with carbon monoxide and hydrogen at elevated temperatures and under superatmospheric pressure in the presence of rhodium carbonyl complexes and of organic solvents which are inert under the reaction conditions, and the reaction mixture thus obtained is then treated, without removing the rhodium catalysts, with molecular oxygen or gases containing molecular oxygen, in the presence of lower fatty acids, and the mixture of 4-acyloxy-n-butyric acid and 3-acyloxy-iso-butyric acid thus obtained is passed, as a vapor, at from 150° to 500°C, over aluminum oxide, titanium oxide, silicon dioxide, silicates of metals of main groups 1 to 3 of the periodic table or active charcoal.

It is an advantage of the new process that it gives good yields and that two valuable products are obtained simultaneously. It is a further advantage that the process can be easily scaled up to industrial operation. It is yet a further advantage that the process starts from allyl esters which are easily manufactured from inexpensive propylene. Finally, it is an advantage of the new process that it does not give waste by-products such as ammonium sulfate.

The preferred starting materials are allyl esters of fatty acids of up to 4 carbon atoms, for example allyl acetate, allyl propionate, allyl butyrate or allyl formate. Allyl acetate has proved particularly important industrially.

Carbon monoxide and hydrogen are advantageously used for the hydroformylation in a volume ratio of from 1 : 0.5 to 1 : 2, and preferably in approximately equimolecular amounts. As a rule, at least stoichiometric amounts of the gas mixture are used, but it is advantageous to employ an excess, e.g. up to 100 mole percent, based on the allyl esters used.

The hydroformylation is expediently carried out at from 60° to 150°C. Temperatures of from 70° to 120°C and pressures of from 80 to 700 atmospheres, especially from 150 to 350 atmospheres, have proved particularly suitable.

The hydroformylation is carried out in the presence of rhodium carbonyl complexes. Though the precise composition of the catalytic rhodium carbonyl complexes is not known, it is assumed that they are rhodium carbonyl or rhodium carbonyl-hydride. Accordingly, rhodium carbonyl can be used directly as a catalyst, but in industrial operation it is preferred to allow the catalytic rhodium carbonyl complexes to form the starting materials during the reaction. Examples of starting materials used are rhodium chloride, rhodium carbonyl-chloride, cyclooctadienyl-rhodium chloride, dicarbonyl-rhodium acetonylacetonate and fatty acid salts of rhodium. In the presence of carbon monoxide under the reaction conditions, these compounds give catalytic rhodium carbonyl complexes. The amount of rhodium used is advantageously from 5 to 500 ppm, in particular from 20 to 200 ppm, calculated as metal and based on reaction mixture employed.

The hydroformylation is carried out in the presence of liquid solvents which are inert under the reaction conditions. Examples of suitable solvents are saturated hydrocarbons boiling at from 30° to 150°C, especially at from 40° to 140°C, such as cyclohexane, hexane, benzene or toluene, or ethers such as diethyl ether, dibutyl ether, tetrahydrofuran or dioxane. The above hydrocarbons are preferred as solvents. Advantageously, the amount of solvent used is such that the starting mixture contains from 10 to 50 percent by weight, in particular from 20 to 40 percent by weight, of allyl ester. The use solvents, especially of the hydrocarbons mentioned, is noteworthy in that it prevents the elimination of fatty acid from the hydroformylation product and hence the formation of undesired by-products such as methacrolein and isobutyraldehyde.

The reaction mixture thus obtained is treated with molecular oxygen, or gases containing molecular oxygen, without first removing the rhodium catalysts. Suitable gases containing oxygen are, e.g. those with from 15 to 25 percent by volume of molecular oxygen; in particular air may be used. In addition to molecular oxygen, they may contain inert gases, such as nitrogen or carbon dioxide. It is preferred to use from 8 to 200 parts by volume of molecular oxygen per part by weight of reaction mixture.

The treatment is preferably carried out at from 20° to 80°C, and temperatures of from 25° to 60°C have proved particularly suitable. As a rule, the reaction is carried out at atmospheric pressure or slightly above, e.g. at up to 5 atmospheres.

The treatment with molecular oxygen or gases containing molecular oxygen is carried out in the presence of lower fatty acids, especially of up to 4 carbon atoms. Examples of suitable fatty acids are acetic acid, propionic acid or butyric acids, but acetic acid is particularly suitable.

The above carboxylic acids are preferably used in amounts of from 0.1 to 100 mole percent, especially from 1 to 50 mole percent, based on the rhodium employed.

The oxidized reaction mixture thus obtained is advantageously freed from the residue containing the catalyst by distillation. The residue containing rhodium can be reused directly for the hydroformylation. Fractional distillation of the reaction mixture gives a mixture of 4-acyloxy-n-butyric acid and 3-acyloxy-isobutyric acid. The ratio of straight-chain to branched isomer is as a rule from 1 : 2 to 1 : 3.

This mixture of 4-acyloxy-n-butyric acid and 3-acyloxy-iso-butyric acid is then vaporized, advantageously under reduced pressure, e.g. at from 200 to 20 mm Hg, and at temperatures of from 150° to 250°C. The vapor mixture is then passed, at from 150° to 500°C, in particular at from 250° to 400°C, over aluminum oxide, titanium dioxide, silicon dioxide, silicates of metals of main groups 1 to 3 of the periodic table or active charcoal as the catalyst. These catalysts may be used either in a fluidized bed or in a fixed bed. It has proved advantageous to use from 0.1 to 2 kg/hour of the vapor of the starting mixture per kilogram of catalyst. The product mixture is cooled and gives a condensate of fatty acid, methacrylic acid and butyrolactone, from which pure butyrolactone and pure methacrylic acid are obtained by conventional methods, e.g. fractional distillation. The fatty acids obtained can be re-used to manufacture allyl esters or can be used in the oxidation stage.

The butyrolactone manufactured by the process of the invention can be used as a solvent. The methacrylic acid obtained is used, as such or after esterification with lower alkanols, as a monomer for the manufacture of polymers.

EXAMPLE 200 g of allyl acetate, 600 g of petroleum ether and 140 mg of rhodium trioxide are introduced into a 2 l high pressure vessel and are hydroformylated with an equimolecular mixture of carbon monoxide and hydrogen at 80°C and from 250 to 300 atmospheres. The reaction has ended after 2 hours, and on cooling and releasing the pressure, a reaction mixture which separates into the phases is obtained; each phase is separately treated with molecular oxygen after addition of 5 ml of acetic acid. This stage is carried out by passing 6 l/hour of molecular oxygen through 100 ml of the particular phase, whilst ensuring good mixing. During the first 4 hours, the remainder of the particular phase is allowed to run in at from 25° to 30°C, and the reaction is then continued for 3 hours at from 35° to 40°C. The end of the reaction can be ascertained from the fact that the gas absorption ceases and the temperature drops. Distillation of the two phases gives a total of 248 g of distillate which contains 29 percent by weight of 4-acetoxy-n-butyric acid and 71 percent of 3-acetoxy-isobutyric acid.

170 g of the mixture of 4-acetoxy-n-butyric acid and 3-acetoxy-isobutyric acid, thus obtained, are vaporized at 50 mm Hg and 200°C and the vapors are then passed over 200 ml of aluminum oxide (particle size 0.2 to 0.3 mm) at from 290° to 300°C. On cooling the reaction mixture, 164 g of a mixture of acetic acid, methacrylic acid and butyrolactone are obtained, which on fractional distillation gives 64 g of methacrylic acid and 26 g of butyrolactone. Only a small amount of residue is left in the vaporizer.

It is also noteworthy that neither acetic acid nor methacrolein nor isobutyraldehyde are detectable by gas chromatography in the reaction mixture after the hydroformylation. Even if the hydroformylation is carried out for 8 hours, no acetic acid is eliminated.

COMPARATIVE EXPERIMENT I 200 g of allyl acetate, 600 ml of hexane and 280 mg of rhodium trioxide are introduced into a high pressure vessel and hydroformylated with an equimolar mixture of carbon monoxide and hydrogen for 2 hours at from 80° to 85°C and 300 atmospheres. After cooling, and releasing the pressure, the lower phase obtained is oxidized without addition of acetic acid. After 12 hours, the conversion is only 65 percent.

COMPARATIVE EXPERIMENT II

The procedure followed is as in the example illustrating the process of the invention, but after the hydroformylation a mixture of 4-acetoxy-n-butyraldehyde and 3-acetoxy-isobutyraldehyde boiling at from 36° to 42°C at 0.1 mm Hg is isolated from the reaction mixture by distillation. 130 g of this product are mixed with 80 g of benzene and 0.24 g of cobalt stearate and 8 l/hour of oxygen are passed into this mixture at 30°C for 4 hours. Distillation of the reaction mixture gives 108 g of a mixture of acetoxy-butyric acids. 130 g of this mixture are vaporized at 50 mm Hg and 200°C and the vapors are passed over 200 ml of aluminum oxide at from 290° to 300°C.

In contrast to the example illustrating the process of the invention, 6 g of a black residue remain in the vaporizer.

We claim:

1. A process for the manufacture of methacrylic acid and butyrolactone, wherein allyl esters of lower fatty acids are hydroformylated by a conventional method with carbon monoxide and hydrogen at elevated temperatures and under superatmospheric pressure in the presence of rhodium carbonyl complexes and of liquid organic solvents which are inert under the reaction conditions, and the reaction mixture thus obtained is then treated, without removing the rhodium catalysts, with molecular oxygen or gases containing molecular oxygen at 20°-80°C at atmospheric to five atmospheres pressure in the presence of lower fatty acids, and the mixture of 4-acyloxy-n-butyric acid and 3-acyloxy-iso-butyric acid thus obtained is passed, as a vapor, at from 150° to 500°C, over aluminum oxide, titanium dioxide, silicon dioxide, silicates of metals of main groups 1 to 3 of the periodic table or active charcoal, as the catalyst.

2. A process as claimed in claim 1, wherein the hydroformylation is carried out in the presence of saturated hydrocarbons boiling at from 40° to 140°C, in such amounts that the starting mixture contains from 10 to 50 percent by weight of allyl ester.

3. A process as claimed in claim 1, wherein the treatment with molecular oxygen or gases containing molecular oxygen is carried out in the presence of from 0.1 to 100 mole percent, based on the rhodium employed, of a fatty acid of up to 4 carbon atoms.

4. A process as claimed in claim 1, wherein aluminum oxide or titanium dioxide is used as the catalyst.

5. A process as claimed in claim 1 wherein the treatment with oxygen or gases containing molecular oxygen is carried out at 25° to 60°C.

6. A process as claimed in claim 1 wherein the treatment with molecular oxygen or gases containing molecular oxygen is carried out at atmospheric pressure, and said mixture of said acids are passed, as a vapor, over said catalyst at a pressure of 20-200mm Hg.

7. A process as claimed in claim 1 wherein said mixture of said acids are passed, as a vapor, over said catalyst at a pressure of 20-200mm Hg.

8. A process as claimed in claim 1 wherein the hydroformylation is carried out at 60°-150°C and 80-700 atmospheres pressure.

* * * * *